(12) United States Patent
Sobrado Marinho

(10) Patent No.: US 8,790,117 B2
(45) Date of Patent: Jul. 29, 2014

(54) BIONIC DEVICE OF MASTICATION SENSITIVITY AND OF MANDIBULAR OCCLUSION

(75) Inventor: Jorge Serafim Sobrado Marinho, Oporto (PT)

(73) Assignee: Clínica Médica Santo António de Joane, LDA., Porto (PT)

( * ) Notice: Subject to any disclaimer, the term of this patent is extended or adjusted under 35 U.S.C. 154(b) by 236 days.

(21) Appl. No.: 13/256,778

(22) PCT Filed: Dec. 9, 2009

(86) PCT No.: PCT/IB2009/055607
§ 371 (c)(1),
(2), (4) Date: Nov. 28, 2011

(87) PCT Pub. No.: WO2010/106401
PCT Pub. Date: Sep. 23, 2010

(65) Prior Publication Data
US 2012/0064486 A1 Mar. 15, 2012

(30) Foreign Application Priority Data
Mar. 16, 2009 (PT) .......................................... 104438

(51) Int. Cl.
*A61C 8/00* (2006.01)
(52) U.S. Cl.
USPC ............................. 433/173; 600/587; 623/24
(58) Field of Classification Search
USPC ..................... 433/173–176; 128/848; 623/24; 600/590, 587
See application file for complete search history.

(56) References Cited

U.S. PATENT DOCUMENTS 5,078,153 A 1/1992 Nordlander et al.

FOREIGN PATENT DOCUMENTS

| DE | 3444780 A1 | 6/1986 |
| JP | 2008-272322 A | 11/2008 |
| WO | 94/28828 A1 | 12/1994 |

OTHER PUBLICATIONS

Wim Claes et al.; "A 136-mu W/Channel Autonomous Strain-Gauge Datalogger"; IEEE Journal of Solid-State Circuits, IEEE Service Center, Piscataway, NJ, US; vol. 38, No. 12, Dec. 1, 2003; pp. 2280-2287; XP011104271.
International Search Report for PCT/IB2009/055607 dated Apr. 7, 2010.

*Primary Examiner* — Sunil K Singh
(74) *Attorney, Agent, or Firm* — John P. White; Cooper & Dunham LLP

(57) ABSTRACT

The presently disclosed subject matter has application in the fields of Medicine, Neurology, Stomatology, Dentistry, Maxillofacial Surgery and Gerontology, using electronics nanotechnology and biomechanics technologies. The disclosed subject matter includes a bionic device of transduction of the mastication pressure into an electrical stimulus, capable of being perceived by the organism in the form of a nociceptive stimulus, which triggers in the organism an appropriate motor response of defense or decrease of muscle contraction. A generating device of nociceptive stimulus able to stimulate the brain areas related to chewing can be provided, modulating the muscular response thus avoiding the problems of overload during the process of mastication or while sleeping, involuntary movements called parafunctions of mastication, which translates to sharply wear down the dental crowns, also called bruxism. An exemplary embodiment can include a driver, interface with the nervous structures, prosthetic abutment, and processing device and force transducer.

17 Claims, 3 Drawing Sheets

BIONIC DEVICE OF MASTICATION SENSITIVITY AND OF MANDIBULAR OCCLUSION

This application is a U.S. national phase filing under 35 U.S.C. §371 of PCT Application No. PCT/IB2009/055607 filed Dec. 9, 2009, claiming priority under 35 U.S.C. §119 to Portuguese patent application No. 104438, filed Mar. 16, 2009, the entire disclosures of which are hereby incorporated by reference herein.

TECHNICAL ASPECTS OF THE INVENTION

This invention has applications in the fields of Medicine, Neurology, Stomatology, Dentistry, Maxillofacial Surgery and Gerontology, allowing the restoration of proprioceptive and tactile sensitivity in mastication, as well as improving the balance capabilities and stereotaxy in edentulous or partial edentulous individuals. Using Nanotechnology, Microelectronics, Bionics and Biophysics technologies.

BACKGROUND OF THE INVENTION

The document DE3444780 advocates the use of a dental implant constituted of three layers of material, namely: 1—Titanium as its core, 2—Intermediate surface coating consisting of bioactive ceramic and 3—Carbon fibers, fixed to the outer surface of the bioactive ceramic. The inventor states that the sensitivity given by the implant comes from the bone transmission of the loads received by the implant, and distributed to the periphery of the bone by filaments of the carbon fiber.

The invention which is intended to be presented is based on the concept of using any type of implant therefore it is not necessary to produce implants with specially designed surfaces to provide sensitivity to the mastication and dental occlusion forces.

The sensitivity is transmitted by an electrical pulse generated in a structure that is fixed to the head of the implant, (ahead referred as abutment) and lodging inside a bionic mechanism that converts a compressive force into an electrical pulse which can be perceived by the nervous endings of the trigeminal nerve.

The invention which it is intended to present also has a structural advantage that can be used in any type of implant independently of its brand, already osseointegrated or to be implanted, because: 1—There is no need to change the production line to make implants with particular surface features designed for sensitive teeth. 2—The Abutment with the bionic device that generates the electrical pulse for nerve stimulation can be installed at any time after the placement of an implant prior and after the osseointegration having been verified The invention which is intended to be presented has the functional advantage of generating an electrical pulse of nerve proprioceptive stimulation whose magnitude is directly related to the intensity of the masticatory forces of occlusion.

There are today several procedures for teeth replacement based on dental implants technology, which can be divided into two major groups: 1—Removable prostheses over implants are used during the day and removed after the meals and before bedtime. The connectors that attach them to the implants have only the purpose of allowing a minimum of stability and security during phonation, breathing, and mastication. The forces triggered by the mastication work are not transmitted to the implants by the axis of insertion of of the same, but by tangential plans and therefore not perceived through bone conduction. 2—Fixed prostheses over the implants restrained by fixed and permanent devices, such as abutments and screws adapted to the head or base of the implants. These prosthetic devices ensure the solidity of the set prosthesis/implants, and thus the transmission of the mastication forces directly to the structure of the implants, which will dissipate them to the surrounding bone. The bone sensitivity is a vague, imprecise and non discriminating sensitivity, much like the deep visceral abdominal sensitivity. Patients on whom implant supported fixed prostheses were placed, are struggling with the problem of adequating the intensity of the mastication forces to the type of food, its texture and hardness, and sometimes is frequent the phenomenon of overload, which leads to the fatigue of the material used in the manufacture of prostheses, whether in metal and ceramic, acrylic, or totally made of minerals such as zirconium and ceramics. The appearance of micro cracks after some time of use (which will be as fast as the stiffness of the material in question lowers) will lead to the fracture of the materials used, and even in some cases, to structural fractures such as breakage of screws and abutments that lead to permanent damages of implanted supported prosthesis.

The document DE3444780 aims to give a morphological configuration of the tooth root implant in what concerns mobility, strength, and sensitivity to pressure, but has no specific mechanism that ensures the generation, transport and delivery of an electrical stimulus that excites the nerve endings responsible for tooth sensitivity.

The present invention has a bionic device housed in an implant abutment that makes it sensitive to mastication pressure forces (or other forces related thereto). The forces are converted into electrical pulses of suitable magnitude and intensity to be perceived by the nerve endings of the trigeminal nerve. The electrical pulse is carried by a copper conducting wire coated with a biocompatible sheath in a distal platform of which there is a wire mesh of titanium wrapped in polyglyconate sodium and which adapts to the mental nerve endings or infra-orbicular nerve, both are branches of the trigeminal nerve. Thus, it becomes possible to provide the brain feedback information about the magnitude and type of mastication forces that are being developed by the stomatognathic system at that time. This will provide the brain efferent information of regulation and modulation of muscle contraction forces of the stomatognathic system which will save the set implants/fixed prosthesis over implants from the structural stress forces overload, that cause fatigue of the material and the structural microfractures.

The advantages of the invention, over what is already known, are:

1. Dental sensitivity, which is an important function for the control of posture and body balance.

2. The mastication sensitivity had never before been valued by different implant manufacturers, but the sensitivity function of natural teeth contributes, according to current scientific research, to an improved balance and to the preservation of motion in patients over 70 years of age.

3. This invention can be adapted to any implant already on the market and can be placed even in patients who already have implants in the mouth.

4. While the invention DE3444780 is based on the principle of conducting the sensitivity through the bone surrounding the implant, the present invention performs the delivery of an electrical stimulation corresponding to the pressure exerted during mastication, directly on the nerve endings of the trigeminal nerve, allowing a proprioceptive and discriminative sensitivity much more precise than that which is perceived only by bone conduction, being in this case deep undefined visceral sensitivity.

The economic importance of the invention lies in three aspects:

a. Prevents the occurrence of the phenomenon of overload exerted by the forces of mastication on the prosthetic device or on the anatomical replacement devices anchored on the implants. Thus fatigue accidents or structural damage of the material of the whole implant prosthesis set can be avoided. This will decrease the patient's visits to the dental clinic for repairing the installed prostheses.

b. By contributing to a better understanding of texture and hardness of food, one will masticate more effectively with greater satisfaction and pleasure for the patient. The confidence of the patient will increase, and therefore the demand of the techniques of oral rehabilitation with dental implants.

c. By allowing the perception of the relative position of the mandible in relation to the head and body, provides an improved spatial orientation with gains in motion and balance.

SUMMARY

The aim of the present invention comprises providing a bionic sensitivity device of mastication and mandibular occlusion.

The device is characterized by including one or more transducers of mechanical stress of the mandible in an electrical signal suitable for interfacing with the nervous structures.

In one exemplary embodiment of the present invention, the device is characterized by counting at least one transducer of mechanical stress on the jaw into an electrical pulse (5) at least one conducting line of that electrical pulse (1), and at least one interface card for the nervous structures (2).

As is understandable, the transducer can be located in various situations, which include all of the maxillomandibular area, in any type of mechanical supports.

In another embodiment of the present invention, the device is characterized by having at least a transducer of mechanical stress of the dental implant into an electrical pulse (5), also comprising at least one conducting line of that electrical pulse (1), and at least an interface card for the nervous structures (2).

Another embodiment of the present invention further comprises a device for data processing, especially suitable for producing a gradual electrical pulse directly related to the intensity of the mechanical stress, and a source of energy, namely a battery.

In another embodiment of the present invention, the transducer (5) is piezoelectric.

In yet another embodiment of the present invention, the conducting line (1) comprises a copper core (6) insulating coating (7), mainly silicone or polytetrafluoroethylene and bio-compatible coating (8), including a titanium mesh (8).

In yet another embodiment of the present invention, the interface card (2) comprises a neurological compatible membrane in polyglycan or polyglyconate sodium (9), in which are embedded one or more of: copper conductor (10), gold plate (12), plate coated in gold (12), and titanium mesh (11).

Another embodiment of the present invention comprises a universal prosthetic abutment according to any of the previous embodiments and characterized by comprising the bionic device with mastication sensitivity and mandibular occlusion.

Another embodiment of the present invention comprises a dental implant according to any of the previous embodiments and characterized by comprising the bionic device with sensitivity and masticatory mandibular occlusion.

The present invention is, thus, useful in the fields of Medicine, Neurology, Stomatology, Dentistry, Maxillofacial Surgery and Gerontology, and utilizes high-tech Electronic Nanotechnology and Biomechanics technology.

The invention which is now intended to be presented has a structural advantage which can be used in any implant of any brand, already placed into the bone or to be osseointegrated. It is not necessary to change the production line to produce implants with particular surface features, designed for dental sensitivity. The Abutment with the bionic device that generates the electrical pulse for nerve stimulation may be installed at any time after the placement of an implant prior and after the osseointegration having taken place.

The invention which is now intended to be presented has also a functional advantage of generating an electrical pulse of proprioceptive nerve stimulation whose magnitude is directly related to the intensity of the masticatory forces of occlusion. Thus, it becomes possible to provide to the brain information feedback about the magnitude and type of mastication forces that are being developed by the stomatognathic system at that time.

This information provides efferent regulation information to the brain and modulation of muscle contraction forces of the stomatognathic system which would save the whole set of implants/fixed prosthesis on implants to the structural stress forces overload, which are responsible of causing material fatigue and structural microfractures.

The advantages of the invention, over what is already available on the market, also include:

1. Restoring teeth sensitiveness—which is an important function for the control of posture and body balance.

2. Restoring mastication sensitiveness—which contributes to a better balance and preservation of movement in older patients.

3. Adaptable to any implant already on the market—can be placed even in patients who already have implants in the mouth.

4. Delivery of an electrical stimulation corresponding to the pressure exerted during mastication, directly on the nerve endings of the trigeminal nerve—thus allowing a proprioceptive sensibility far more perceptive than that which is perceived only by bone conduction.

5. Prevention of overload—exerted by mastication forces on the prosthetic devices or of the anatomical substitutes that are anchored on the implants, in this way material fatigue accidents or structural joint failure in implant/prosthesis can be avoided and, thus, decreasing dental office visits for repair of installed dentures.

6. Enhanced understanding of texture and hardness of food—allowing a more efficient mastication with greater satisfaction and pleasure for the patient, increasing the confidence of the patient, and therefore the demand of the techniques of oral rehabilitation with dental implants.

DESCRIPTION OF FIGURES

For an easier understanding of the invention we are attaching the figures which represent exemplary embodiments of the invention which, however, are not intended to limit the scope of this invention.

(1) represents the guiding wire of the electrical pulses, (2) represents the interface card with the nervous structures, (3) represents the prosthetic abutment, (4) represents the prosthetic abutment, and (5) represents the processing device and the force transducer.

Figure 1:
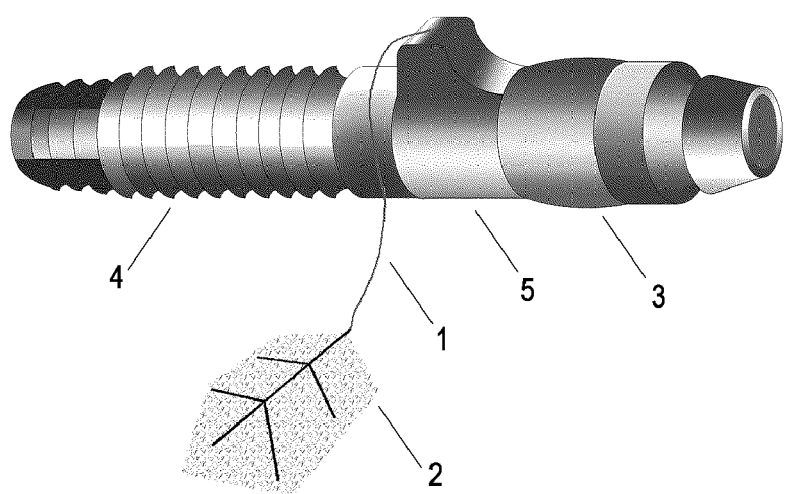
FIG. 1: Schematic representation of the device where.
Figure 2:
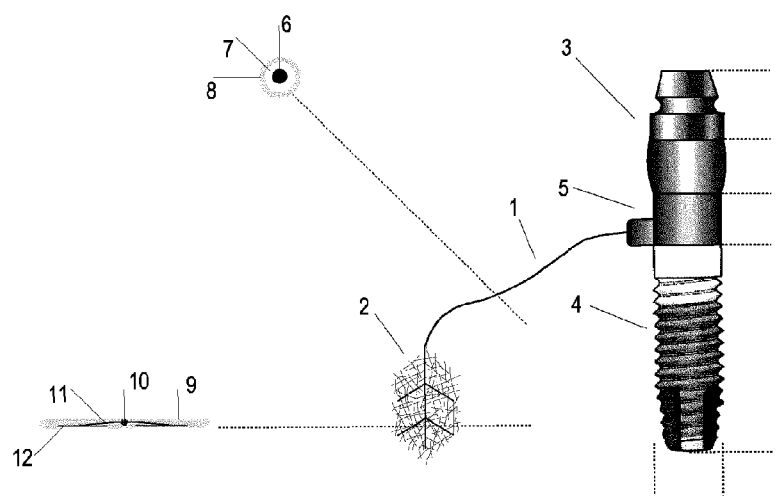

FIG. 2: Detailed schematic representation of the device where:

(1) represents the guiding wire of the electrical pulses, (2) represents the interface card with the nervous structures, (3) represents the prosthetic abutment, (4) represents the prosthetic abutment, (5) represents the processing device and force transducer, (6) represents the core of the guiding wire, namely in copper, (7) represents the insulating coating of the guiding wire, namely in silicone, (8) represents a biocompatible coating of the conducting wire, namely in titanium mesh, (9) represents a neuron-compatible membrane, namely in polyglycan,

(10) represents a bio-compatible mesh, namely in titanium

(11) represents a conductor of the interface card, namely in copper, and

(12) represents a plate, namely in gold or gold-plated.

Figure 3:
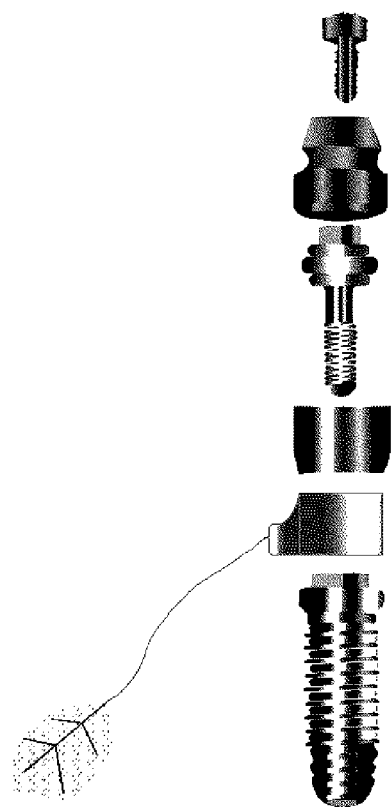

FIG. 3: Schematic representation of the mechanical assembly of the entire device and prosthetic abutment.

DESCRIPTION OF INVENTION

This invention represents a fundamental improvement to the majority of dental implants marketed so far as it brings the anatomical replacement devices (fixed prosthesis over dental implants) close to the primary function of the teeth during mastication, which is to provide information to the brain of the amount of force necessary and sufficient for proper mastication of food intake at a given moment. So far all the technology around the implants, has focused on the phenomenon of osseointegration, the demand for new designs of the profile of the implants, together with the search for new types of surface, allowing a better biocompatibility and therefore a faster osseointegration, have proved useful so far as resolving only the aspect of speed of osseointegration, against the biofunctionality of the set Implant/dental prosthesis. There is still remains the problem of possible overload of the mastication forces because the brain has difficulty in evaluating the hardness of the diet, and thus in sending instructions to the muscles of mastication to apply an appropriate amount of contractile force to the effort of mastication in real time.

Another embodiment of the present invention can consist of or can include 5 five elements: 1—Modified prosthetic abutment possessing proper fit for internal or external connection implants. 2—Micro-chip equipped with a pressure evaluation device, and a data processing device and transduction of mechanical forces into gradual electrical pulses directly related to the intensity scale of masticatory pressure or occlusion. 3—Unit power supply (battery) to feed the operation of the micro-chip. 4—Electrical conducting wire generated in the micro-chip, consisting of 3 layers: a) capillary inner wire of copper or other electrically conductive metal. b) First coating the wire, carried out with inert material and electrically non-conducting (teflon). c) External coating consisting of titanium mesh to be biologically compatible and/or mucus integrable. 5—Interface card with the nervous structures, consisting of a core of radially disposed metal plates and embedded within the polyglycan material.

Explaining the operation of the invention, shall be conducted as follow:

During the normal process of mastication are applied forces on the modified abutment, which are detected by the micro-chip that transforms them in direct relationship with its magnitude, into electrical pulses that are generated in the micro-chip and sent by the conducting wire, to the interface card implemented in the neighborhood of a nerve ending, which will deliver the electrical pulse to the nervous tissue. The nerve ending of a nerve of the V cranial pair, leads the stimulus to the sensitive centers of the V cranial pair where they will be integrated and interpreted corresponding then a motor response to all the muscles of the stomatognathic system.

The most common embodiment of the invention includes the placement of each modified abutments on top of implants located in the four quadrants of the mouth: hemi-maxillary top right hemi-maxilla top left, right hemi-mandible, left hemi-mandible. Thus we will have a device stimulating each of the nerve-endings of the four nervous beams respectively roots V2, V3 right and left of the V cranial pair, or trigeminal nerve.

The technical specifications of the invention comprise:

1. Universal prosthetic abutment, adaptable to any dental implant.

2. Micro-chip residing in the abutment, author of the electrical stimulus adapted in intensity and frequency to the sensory nerve endings of the V Cranial pair.

3. System of transmission of the electrical stimulus through an insulated cable with filiform diameter, ending in a film of noble metal, coated with polyglycan, which will sit directly on the nerve ending of the trigeminal nerve.

Optional features, which are not mandatory for the invention, but which have inventive character or novelty, include:

1. The delayed transport of the electrical stimulus from the outset in the abutment on the implant up to the termination of the roots V2 or V3 of the trigeminal nerve.

2. The chip that converts the forces of pressure into electrical stimulus with amplitude and frequency modulated to be perceived by the nerve endings.

3. The possibility of placing the chip on abutments "ad novo" on already installed implants in the oral cavity.

The invention claimed is:

1. Bionic device sensitive to mastication and mandibular occlusion comprising:

a transducer that transforms mechanical stress on the jaw into an electrical pulse, guiding wire for the electrical pulse, and an interface card to nervous endings, suitable for interfacing to the trigeminal nerve, wherein the interface card includes a neuron-compatible membrane in polyglycon or polyglyconate sodium, in which are embedded one or more of: copper conductor, plate gold, plate coated in gold, and titanium mesh.

2. Bionic device according to claim 1 wherein the transducer that transforms the mechanical stress into an electrical pulse, the guiding wire of the electrical pulse, and the interface card to nervous endings, is configured such that said mechanical stress is from the occlusion of the jaw from posture and balance of the human body.

3. Bionic device according to claim 1, further comprising a device for data processing, which modulates an electrical pulse directly related in frequency and/or amplitude to the intensity of mechanical stress.

4. Bionic device according to claim 1, wherein the transducer is piezoelectric.

5. Bionic device according to claim 1, wherein the guiding wire includes a conducting wire with a copper core, insulating coating, and bio-compatible coating.

6. Bionic device according to claim 5, wherein the insulating coating includes silicone or polytetrafluoroethylene, and the bio-compatible coating includes a titanium mesh.

7. A universal prosthetic abutment comprising the bionic device sensitive to mastication and mandibular occlusion, according to claim 1.

8. A dental implant comprising the bionic device sensitive to mastication and mandibular occlusion, according to claim 1.

9. Bionic device according to claim 2, further comprising a device for data processing, which modulates an electrical pulse directly related in frequency and/or amplitude to the intensity of mechanical stress.

10. Bionic device according to claim 2, wherein the transducer is piezoelectric.

11. Bionic device according to claim 3, wherein the transducer is piezoelectric.

12. Bionic device according to claim 2, wherein the guiding wire includes a conducting wire with a copper core, insulating coating, and bio-compatible coating.

13. Bionic device according to claim 3, wherein the guiding wire includes a conducting wire with a copper core, insulating coating, and bio-compatible coating.

14. A universal prosthetic abutment comprising the bionic device sensitive to mastication and mandibular occlusion, according to claim 2.

15. A universal prosthetic abutment comprising the bionic device sensitive to mastication and mandibular occlusion, according to claim 3.

16. A dental implant comprising the bionic device sensitive to mastication and mandibular occlusion, according to claim 2.

17. A dental implant comprising the bionic device sensitive to mastication and mandibular occlusion, according to claim 3.

* * * * *